(12) United States Patent
Klug et al.

(10) Patent No.: US 7,709,011 B2
(45) Date of Patent: *May 4, 2010

(54) COSMETIC OR PHARMACEUTICAL PREPARATIONS COMPRISING AN OXALKYLATED POLYGLYCEROL ESTER

(75) Inventors: Peter Klug, Grossostheim (DE); Franz Xaver Scherl, Burgkirchen (DE)

(73) Assignee: Clariant Produkte (Deutschland) GmbH, Sulzbach (DE)

( * ) Notice: Subject to any disclaimer, the term of this patent is extended or adjusted under 35 U.S.C. 154(b) by 1163 days.

This patent is subject to a terminal disclaimer.

(21) Appl. No.: 10/387,608

(22) Filed: Mar. 13, 2003

(65) Prior Publication Data

US 2003/0235598 A1  Dec. 25, 2003

(30) Foreign Application Priority Data

Mar. 16, 2002  (DE)  ............................... 102 11 801

(51) Int. Cl.
A61K 9/00 (2006.01)
A61K 8/02 (2006.01)

(52) U.S. Cl. .................... 424/400; 424/401; 514/941

(58) Field of Classification Search ............... 424/78.03, 424/400, 401; 514/941
See application file for complete search history.

(56) References Cited

U.S. PATENT DOCUMENTS

| | | | |
|---|---|---|---|
| 2,679,520 A | 5/1954 | de Groote | |
| 4,265,774 A | 5/1981 | Langdon | |
| 4,614,622 A | 9/1986 | Huettinger et al. | |
| 4,774,017 A | 9/1988 | Seibert et al. | 252/174.12 |
| 4,853,026 A | 8/1989 | Frisch et al. | |
| 4,895,681 A * | 1/1990 | Herrmann et al. | 554/223 |
| 4,977,030 A | 12/1990 | Hotta et al. | 428/447 |
| 5,026,800 A | 6/1991 | Kimura et al. | |
| 5,192,462 A | 3/1993 | Gloor et al. | 252/174.21 |
| 5,597,551 A | 1/1997 | Malawer et al. | |
| 5,750,468 A | 5/1998 | Wright et al. | |
| 5,858,921 A | 1/1999 | Magin et al. | |
| 5,912,208 A | 6/1999 | Hioki | |
| 6,368,581 B1 | 4/2002 | Karlen et al. | |
| 6,369,851 B1 | 4/2002 | Marflak et al. | |
| 2002/0013494 A1 | 1/2002 | Carpenter | |
| 2002/0035047 A1 | 3/2002 | Sebillotte-Arnaud | |
| 2003/0235596 A1 | 12/2003 | Klug et al. | |
| 2004/0072916 A1* | 4/2004 | Leinweber et al. | 516/135 |
| 2004/0143057 A1 | 7/2004 | Ahrens et al. | |
| 2005/0037926 A1 | 2/2005 | Zerrer | |
| 2006/0166826 A1 | 7/2006 | Zerrer et al. | |

FOREIGN PATENT DOCUMENTS

| | | |
|---|---|---|
| CA | 2 451 237 | 1/2003 |
| DE | 20 24 051 A1 | 12/1971 |
| DE | 32 39 564 C1 | 5/1984 |
| DE | 34 46 720 A1 | 6/1986 |
| DE | 37 26 015 | 2/1988 |
| DE | 195 05 178 A1 | 8/1996 |
| DE | 199 36 092 A1 | 2/2001 |
| DE | 101 24 547 | 11/2002 |
| EP | 0 264 826 | 4/1988 |
| EP | 0 349 240 | 1/1990 |
| EP | 0 379 852 | 8/1990 |
| EP | 0807429 | 11/1997 |
| EP | 1 055 407 A | 11/2000 |
| EP | 1 344 518 A2 | 9/2003 |
| GB | 1 333 475 | 10/1973 |
| GB | 2129004 | 11/2007 |
| JP | 54 163984 | 6/1978 |
| JP | 58 196258 | 2/1984 |
| JP | 59-087035 | * 5/1984 |
| JP | 60 212480 | 10/1985 |
| JP | 61-130208 | 6/1986 |
| JP | 61 130208 A | 6/1986 |
| JP | 62153255 | * 7/1997 |
| JP | 2001 139795 | 9/2001 |
| WO | WO 96/25215 | 8/1996 |
| WO | 9730691 | 8/1997 |
| WO | WO 98/06259 | 2/1998 |
| WO | WO 99/05914 | 2/1999 |
| WO | WO 01/08481 | 2/2001 |
| WO | WO-02066136 | * 8/2002 |
| WO | WO 02/089575 | 11/2002 |
| WO | WO 03/000055 | 1/2003 |
| WO | WO 03/063818 | 8/2003 |

OTHER PUBLICATIONS

English abstract for WO 01/08481, Feb. 8, 2001.
English abstract for DE 10124547, Nov. 28, 2002.
English Language Translation of Japanese Patent Application Publication No. Sho-62-153225 (KUBO), Published Jul. 8, 1987.
English Language Abstract for JP2000-344637, Dec. 12, 2000, to Wella (See USP#2).

(Continued)

*Primary Examiner*—Alton N Pryor
(74) *Attorney, Agent, or Firm*—Tod A. Waldrop

(57) ABSTRACT

Cosmetic or pharmaceutical preparations comprising an oxalkylated polyglycerol ester of the formula (1)

$$B-(OA)_x-O-\left[CH_2CH-CH_2-O\right]_n-(AO)_y-B \quad (1)$$
$$\underset{|}{O}$$
$$\underset{|}{(AO)_z}-B$$

in which A is a group of the formula $-C_2H_4-$ or $-C_3H_6-$,
B is hydrogen or a group of the formula $-COR$,
where at least one symbol B is a group of the formula $-COR$,
R is $C_7-C_{21}$-alkyl or
$C_2-C_{21}$-alkenyl, n is a number from 1 to 30 and x, y and z are numbers from 0 to 100, where the sum of x, y and z is 50 to 250.

6 Claims, No Drawings

OTHER PUBLICATIONS

English Language Abstract for JPH-11-509863T, Aug. 28, 1997, to Unilever (See FPD# 1).
English Language Abstract for JPH07-215842, Aug. 15, 1995, to Shiseido Co.
English Language Abstract for JPH05-345707, Dec. 27, 1993, to Helene Curtis.
English Language Abstract for JP2001-513768T, Sep. 4, 2001 (See USPAP#2).
English Language Abstract for JP-H04-224507, Aug. 13, 1994, to Kose.
English Language Abstract for JP-H06-279262, Apr. 10, 1994, to Shiseido Co.
English Language Abstract for JP-2001-139796, May 22, 2001, to Pigeon.
English Language Abstract for JP-H10-045533, 1998-02-1712-12, to Unilever (See FPD#3).
English Language Abstract for JP-H07-101847, Apr. 18, 1995, to Shiseido.
English Language Abstract for JP-S59-087035, May 19, 1984, to Kawaken
English Language Translation of JP Sho-62-153225, Kubo et al., Jul. 8, 1987.
English abstract for JP 2002-047173, dated Jul. 13, 2000.
English abstract for JP 61-130208, dated Jun. 18, 1986.
English abstract for DE 195 05 178 A1, Aug. 22, 1996.
English abstract for DE 34 46 720 A1, Jun. 26, 1986.
English abstract for JP 54 163984, Jun. 16, 1978.
English abstract for JP 58 196258, Feb. 15, 1984.
English abstract for JP 60 212480, Oct. 24, 1985.
English abstract for JP 61 130208 A, Jun. 18, 1986.
English abstract for JP 2001 139796, Sep. 3, 2001.
English abstract for WO 96/25215, Aug. 22, 1996.
English abstract for WO 03/063818, Aug. 7, 2003.
English Abstract for DE 199 36 092 A1, Feb. 1, 2001.
EPO Search Report for EP 03004624, dated Mar. 30, 2003.

* cited by examiner

COSMETIC OR PHARMACEUTICAL PREPARATIONS COMPRISING AN OXALKYLATED POLYGLYCEROL ESTER

Consumer wishes and rheology of cosmetic products are closely related. First, for example, the visual appearance of a cream or lotion is influenced by the viscosity. The sensory properties, such as consistency or spreadability, determine the individual profile of a cosmetic product. The effectiveness of active substances (e.g. sunscreen filters) and also the storage stability of the formulation is also closely related to the rheological properties of the product. In the cosmetics sector, the thickeners and gel formers therefore play a major role.

A number of patent specifications describe the use of polyether esters as thickeners. The prior art is the use of fatty acid esters of long-chain polyethers, for example of polyethylene glycol 6000 distearate. U.S. Pat. No. 4,774,017 describes polyethylene glycol polypropylene glycol monethers as consistency-imparting component, and DE 37 26 015 describes the reaction products of polyalcohols with fatty acids, for example pentaerythritol fatty acid esters and their thickening action. U.S. Pat. No. 5,129,462 describes shampoo formulations comprising polyethylene glycol polyol fatty acid esters, in particular PEG pentaerythritol fatty acid esters as thickeners. The processing and ability of this class of compound to be formulated is impaired by their high melting points or setting points. DE 101 24 547 and WO 01/08481 describe the use of alkoxylated polyglycerol esters as emulsifiers in emulsion polymerization and the use in pesticide preparations.

The invention provides cosmetic and pharmaceutical preparations comprising an oxalkylated polyglycerol ester of the formula (1)

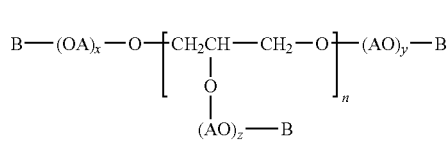

in which A is a group of the formula —$C_2H_4$— or —$C_3H_6$—, B is hydrogen or a group of the formula —COR, where at least one symbol B is a group of the formula —COR, R is $C_7$-$C_{21}$-alkyl, $C_7$-$C_{21}$-hydroxyalkyl or $C_2$-$C_{21}$-alkenyl, n is a number from 1 to 30 and x, y and z are numbers from 0 to 100, where the sum of x, y and z is 50 to 250.

Compared with the prior art, for example PEG 6000 distearate, alkoxylated polyglycerol esters according to formula (1) have improved thickener performance and have a lower setting point, which is of great advantage from an applications point of view. They are predominantly soft waxes which, with further components, for example water, polyhydric alcohols, in particular glycols, such as propylene glycol, butylene glycol, hexylene glycol, polyethylene glycol, alkoxylated alcohols having $C_1$-$C_{22}$-alkyl radicals and 1 to 50 EO or PO units, ethoxylated partial glycerides, for example PEG-7 glyceryl cocoate and glycerol, produce flowable, easy-to-handle products.

These oxalkylated polyglycerol esters are prepared either by oxyalkylation of a polyglycerol and subsequent esterification, or by esterification of the polyglyerol and subsequent oxalkylation.

The alkoxylated polyglycerol esters used according to the invention are prepared in two or more reaction stages. The synthesis of the polyglycerols or oligoglycerols, diglycerol, triglycerol, tetraglycerol to decaglycerol takes place in a known manner by polycondensation of glycerol in the presence of catalysts, for example reducing phosphoric acids, alkali metal hydroxides, alkali metal carbonates, alkali metal bicarbonates, alkali metal alkoxylates and alkoxides at temperatures of from 190° C. to 270° C. With the discharge of water of condensation, the formation of the polyglycerols takes place within 8 to 72 hours. The hydroxyl number (OH number) of such as reaction mixture is, for example, 1072 mg of KOH/g of an oligomer mixture, for which corresponds, on average, to a polyglycerol-4. The number n, being a measure of the degree of condensation, is preferably between 1.5 and 10, in particular between 1.8 and 5.

The alkoxylation, in particular the ethoxylation, of the polyglycerols or oligoglycerols takes place at 130 to 190° C., preferably 160° C., in the presence of a basic catalyst, for example NaOH, after drying at 100° C. and a vacuum of 20 mbar (about 0.5 hours), where alkoxide, preferably ethylene oxide, is metered in at a pressure of from 1 bar to 6 bar, in particular at 4 bar to 6 bar, over the course of 15 hours. The resulting ethoxylated polyglycerols or oligoglycerols have a total degree of EO (x+y+z) of from 50 to 250, preferably 100 to 200, particularly preferably 130 to 170, based on the average molecular mass of the polyglycerol.

The prepared ethoxylated poly/oligoglycerol is, after cooling the reaction mixture to 60-100° C., treated with a catalyst, e.g. alkylbenzenesulfonic acid and, through the addition of acid, preferably hypophosphorous acid or phosphoric acid, the pH is adjusted to 4-5 (10% aqueous). Esterification is then carried out by adding a fatty acid, for example stearic acid, isostearic acid, 12-hydroxystearic acid, coconut fatty acid, lauric acid, oleic acid or alkyl esters thereof, chlorides or anhydrides, at a reaction temperature of from 160 to 230° C. and a reaction time of from 10 to 35 hours. The molar fraction of fatty acid or fatty acid derivatives can be chosen as desired, but at least one OH group of the oxalkylated polyglycerol must be esterified.

The preparation method of these alkoxylated poly/oligoglycerol fatty acid esters can also be varied such that the poly/oligoglycerols are firstly esterified with fatty acid in the corresponding molar ratio and then alkoxylated.

As a result of this preparation process, the polyglycerols derivatives used according to the invention are mixtures of compounds of the abovementioned formula with varying value for n, i.e. mixtures with a content of monoglycerol ester are also suitable.

These polyglycerol esters are suitable as thickeners and dispersants for aqueous, aqueous-alcoholic and aqueous-surface-active preparations and as emulsifiers, suspending agents with a thickening action and bodying agents for emulsions and suspensions.

The preparations, emulsions and suspensions are cosmetic and pharmaceutical compositions, such as, for example, shampoos, shower preparations, shower gels, foam baths, gels, lotions, creams and ointments.

Based on the finished formulation, the preparations, emulsions and suspensions according to the invention comprise preferably 0.05 to 10% by weight, particularly preferably 0.1 to 5% by weight, especially preferably 0.5 to 3% by weight, of the described alkoxylated polyglycerol esters.

The compositions according to the invention can comprise, as further auxiliaries and additives, all customary anionic, cationic, zwitterionic, nonionic and amphoteric surfactants, and further additives customary in cosmetics, such as, for example, superfatting agents, stabilizers, biogenic active ingredients, glycerol, preservatives, pearlizing agents, dyes and fragrances, solvents, opacifiers, further thickeners and dispersants, and also protein derivatives such as gelatin, collagen hydrolysates, natural- and synthetic-based polypeptides, egg yolk, lecithin, lanolin and lanolin derivatives, fatty alcohols, silicones, deodorizing agents, substances with a keratolytic and keratoplastic action, enzymes and carrier substances. In addition, antimicrobially effective agents may be added to the compositions according to the invention.

The total amount of the surfactants used in the compositions according to the invention can, based on the finished composition, be between 5 and 70% by weight, preferably between 10 and 40% by weight, particularly preferably between 12 and 35% by weight, based on 100% of active substance.

Anionic washing-active substances which may be mentioned are: $(C_{10}$-$C_{20})$-alkyl and alkylene carboxylates, alkyl ether carboxylates, fatty alcohol sulfates, fatty alcohol ether sulfates, alkylamide sulfates and -sulfonates, fatty acid alkylamide polyglycol ether sulfates, alkanesulfonates and hydroxyalkanesulfonates, olefinsulfonates, acyl esters of isethionates, $\alpha$-sulfo fatty acid esters, alkylbenzenesulfonates, alkylphenol glycol ether sulfonates, sulfosuccinates, sulfosuccinic monoesters and diesters, fatty alcohol ether phosphates, protein/fatty acid condensation products, alkyl monoglyceride sulfates and sulfonates, alkyl glyceride ether sulfonates, fatty acid methyl taurides, fatty acid sarcosinates, sulforicinoleates and acyl glutamates. These compounds and their mixtures are used in the form of their water-soluble or water-dispersible salts, for example the sodium, potassium, magnesium, ammonium, mono-, di- and triethanolammonium and analogous alkylammonium salts.

The proportion by weight of the anionic surfactants in the compositions according to the invention is preferably in the range from 7 to 30% by weight, particularly preferably 10 to 25% by weight, especially preferably 12 to 22% by weight.

Suitable cationic surfactants are, for example, quaternary ammonium salts, such as $di(C_{10}$-$C_{24})$-alkyldimethylammonium chloride or bromide, preferably $di(C_{12}$-$C_{18})$-alkyldimethylammonium chloride or bromide; $(C_{10}$-$C_{24})$-alkyldimethylethylammonium chloride or bromide; $(C_{10}$-$C_{24})$-alkyltrimethylammonium chloride or bromide, preferably cetyltrimethylammonium chloride or bromide and $(C_{20}$-$C_{22})$-alkyltrimethylammonium chloride or bromide; $(C_{10}$-$C_{24})$-alkyldimethylbenzylammonium chloride or bromide, preferably $(C_{12}$-$C_{18})$-alkyldimethylbenzylammonium chloride; N—$(C_{10}$-$C_{18})$-alkylpyridinium chloride or bromide, preferably N—$(C_{12}$-$C_{16})$-alkyl-pyridinium chloride or bromide; N—$(C_{10}$-$C_{18})$-alkylisoquinolinium chloride, bromide or monoalkyl sulfate; N—$(C_{12}$-$C_{18})$-alkylpolyoylaminoformylmethylpyridinium chloride; N—$(C_{12}$-$C_{18})$-alkyl-N-methylmorpholinium chloride, bromide or monoalkyl sulfate; N—$(C_{12}$-$C_{18})$-alkyl-N-ethylmorpholinium chloride, bromide or monoalkyl sulfate; $(C_{16}$-$C_{18})$-alkylpentaoxethylammonium chloride; diisobutylphenoxyethoxyethyl-dimethylbenzylammonium chloride; salts of N,N-diethylaminoethylstearylamide and -oleylamide with hydrochloric acid, acetic acid, lactic acid, citric acid, phosphoric acid; N-acylaminoethyl-N,N-diethyl-N-methylammonium chloride, bromide or monoalkyl sulfate and N-acylaminoethyl-N,N-diethyl-N-benzylammonium chloride, bromide or monoalkyl sulfate, where acyl is preferably stearyl or oleyl.

The proportion by weight of the cationic surfactants in the compositions according to the invention is preferably in the range from 1 to 10% by weight, particularly preferably 2 to 7% by weight, especially preferably 3 to 5% by weight.

Suitable nonionic surfactants are, for example: fatty alcohol ethoxylates (alkyl polyethylene glycols); alkylphenol polyethylene glycols; alkyl mercaptan polyethylene glycols; fatty amine ethoxylates (alkylamino polyethylene glycols); fatty acid ethoxylates (acyl polyethylene glycols); polypropylene glycol ethoxylates (Pluronics®); fatty acid alkylolamides (fatty acid amide polyethylene glycols); N-alkyl, N-alkoxypolyhydroxy fatty acid amides, sucrose esters; sorbitol esters and polyglycol ethers.

The proportion by weight of the nonionic surfactants in the compositions according to the invention is preferably in the range from 1 to 20% by weight, particularly preferably 2 to 10% by weight, especially preferably 3 to 7% by weight.

Preferred amphoteric surfactants are: N—$(C_{12}$-$C_{18})$-alkyl-$\beta$-aminopropionates and N—$(C_{12}$-$C_{18})$-alkyl-$\beta$-iminodipropionates as alkali metal and mono-, di- and trialkylammonium salts; N-acylaminoalkyl-N,N-dimethylacetobetaine, preferably N—$(C_8$-$C_{18})$-acylaminopropyl-N, N-dimethylacetobetaine; $(C_{12}$-$C_{18})$-alkyldimethyl-sulfopropylbetaine; amphoteric surfactants based on imidazoline (trade name: Miranol®, Steinapon®), preferably the sodium salt of 1-($\beta$-carboxymethyloxyethyl)-1-(carboxymethyl)-2-laurylimidazolinium; amine oxide, e.g. $(C_{12}$-$C_{18})$-alkyl-dimethylamine oxide, fatty acid amidoalkyl dimethylamine oxide.

The proportion by weight of the amphoteric surfactants in the compositions according to the invention is preferably in the range from 0.5 to 20% by weight, particularly preferably 1 to 10% by weight.

Furthermore, foam-boosting cosurfactants from the groups consisting of alkylbetaines, alkylamidobetaines, aminopropionates, aminoglycinates, imidazoliniumbetaines and sulfobetaines, amine oxides and fatty acid alkanolamides or polyhydroxyamides, can be used in the compositions according to the invention.

Preferred surfactants in the compositions according to the invention are lauryl sulfate, laureth sulfate, cocoamidopropylbetaine, sodium cocoyl glutamate, disodium laureth sulfosuccinate and coconut fatty acid diethanolamide.

The preparations according to the invention can also comprise further additives customary in cosmetics, such as superfatting agents, stabilizers, biogenic active ingredients, glycerol, preservatives, pearlizing agents, dyes and fragrances, solvents, opacifiers, thickeners and dispersants, and also protein derivatives, such as gelatin, collagen hydrolysates, natural- and synthetic-based polypeptides, egg yolk, lecithin, lanolin and lanolin derivatives, fatty alcohols, silicones, deodorizing agents, substances with a keratolytic and keratoplastic action, enzymes and carrier substances. In addition, antimicrobial active agents may be added to the compositions according to the invention.

Super fatting agents which may be used are substances such as, for example, polyethoxylated lanolin derivatives, lecithin derivatives, polyol fatty acid esters, monoglycerides and fatty acid alkanolamides, the latter also serving as foam stabilizers. Typical examples of fats are glycerides, and suitable waxes are, inter alia, beeswax, paraffin wax or microcrystalline waxes, optionally in combination with hydrophilic waxes, e.g. cetylstearyl alcohol.

Stabilizers which may be used are metal salts of fatty acids, such as, for example, magnesium stearate, aluminum stearate and/or zinc stearate. Biogenic active ingredients are understood as meaning, for example, plant extracts and vitamin complexes.

Suitable preservatives are, for example, phenoxyethanol, formaldehyde solution, parabens, pentanediol or sorbic acid.

Suitable pearlizing agents are, for example, glycol distearic esters, such as ethylene glycol distearate, but also fatty acid monoglycol esters.

Dyes that can be used are the substances approved and suitable for cosmetic purposes.

Suitable further thickeners are sodium chloride, potassium chloride, ammonium chloride, sodium sulfate, fatty acid alkylolamides, cellulose derivatives, for example hydroxyethylcellulose, guar gum, polyvinyl alcohol, polyvinylpyrrolidone, hydroxypropyl guar gum, starch and starch and starch derivatives, and natural gums, carboxyvinyl polymers, for example Carbopol 934, 940, 941, 956, 980, 981, 1342, 1382, ethylene glycol esters of fatty acids having 14 to 22, particularly preferably 16 to 22, carbon atoms, in particular mono- and diethylene glycol stearate. Preference is also given to stearin monoethanolamide, stearin diethanolamide, stearin isopropanolamide, stearin monoethanolamide stearate, stearyl stearate, cetyl palmitate, glyceryl stearate, stearamide diethanolamide distearate, stearamide monoethanolamide stearate, N,N-dihydrocarbyl-($C_{12}$-$C_{22}$)—, in particular ($C_{16}$-$C_{18}$)-amidobenzoic acid and soluble salts thereof, N,N-di($C_{16}$-$C_{18}$)-amidobenzoic acid and derivatives thereof.

Based on the finished composition, the dispersants are used in concentrations of from preferably 0.5 to 10% by weight, particularly preferably from 0.5 to 5% by weight, especially preferably from 1 to 4% by weight.

The desired viscosity of the compositions can be set by adding water and/or organic solvents or by adding a combination of organic solvents and thickeners.

In principle, suitable organic solvents are all mono- or polyhydric alcohols. Preference is given to using alcohols having 1 to 4 carbon atoms, such as ethanol, propanol, isopropanol, n-butanol, isobutanol, t-butanol, glycerol and mixtures of said alcohols. Further preferred alcohols are polyethylene glycols with a relative molecular mass below 2000. In particular, a use of polyethylene glycol with a relative molecular mass of between 200 and 600 and in amounts up to 45% by weight and of polyethylene glycol with a relative molecular mass between 400 and 600 in amounts of from 5 to 25% by weight is preferred. Further suitable solvents are, for example, triacetin (glycerol triacetate) and 1-methoxy-2-propanol.

Suitable carrier materials are vegetable oils, natural and hydrogenated oils, waxes, fats, water, alcohols, polyols, glycerol, glycerides, liquid paraffins, liquid fatty alcohols, sterol, polyethylene glycols, cellulose and cellulose derivatives.

The nonaqueous proportion of the emulsions, which is composed largely of the emulsifier, the thickener and the oil body, is usually 5 to 95% by weight, preferably 15 to 75% by weight. It follows from this that the emulsions may comprise 5 to 95% by weight and preferably 25 to 85% by weight of water, depending on whether the intention is to prepare lotions with a comparatively low viscosity or creams and ointments with a high viscosity.

The emulsions can be used as skincare compositions, such as, for example, day creams, night creams, care creams, nutrient cream, body lotions, ointments and the like and comprise, as further auxiliaries and additives, oil bodies, coemulsifiers, super fatting agents, fats, waxes, stabilizers, biogenic active ingredients, glycerol, preservatives, dyes and fragrances.

Suitable oil bodies are, for example, Guerbet alcohols based on fatty alcohols having 6 to 18, preferably 8 to 10, carbon atoms, esters of linear ($C_6$-$C_{13}$)-fatty acids with linear ($C_6$-$C_{20}$)-fatty alcohols, esters of branched ($C_6$-$C_{13}$)-carboxylic acids with linear ($C_6$-$C_{20}$)-fatty alcohols, esters of linear ($C_6$-$C_{18}$)-fatty acids with branched alcohols, in particular 2-ethylhexanol, esters of linear and/or branched fatty acids with polyhydric alcohols (such as, for example, dimerdiol or trimerdiol) and/or Guerbet alcohols, triglycerides based on ($C_6$-$C_{10}$)-fatty acids, vegetable oils, branched primary alcohols, substituted cyclohexanes, Guerbet carbonates, dialkyl ethers and/or aliphatic or aromatic hydrocarbons. The proportion of the oil bodies in the nonaqueous part of the emulsions can constitute 5 to 95% by weight and preferably 15 to 75% by weight.

Suitable nonionogenic coemulsifiers are, inter alia, addition products of from 0 to 30 mol of ethylene oxide and/or 0 to 5 mol of propylene oxide onto linear fatty alcohols having 8 to 22 carbon atoms, onto fatty acids having 12 to 22 carbon atoms, onto alkylphenols having 8 to 15 carbon atoms in the alkyl group and onto sorbitan or sorbitol esters; ($C_{12}$-$C_{18}$)-fatty acid mono- and diesters of addition products of from 0 to 30 mol of ethylene oxide onto glycerol; glycerol mono- and diesters and sorbitan mono- and diesters of saturated and unsaturated fatty acids having 6 to 22 carbon atoms and optionally ethylene oxide addition products thereof; addition products of from 15 to 60 mol of ethylene oxide onto castor oil and/or hydrogenated castor oil; polyol and in particular polyglycerol esters, such as, for example, polyglycerol polyricinoleate and polyglycerol poly-12-hydroxystearate. Likewise suitable are mixtures of compounds of two or more of these classes of substances.

Suitable ionogenic coemulsifiers are, for example, anionic emulsifiers, such as mono-, di- or triphosphoric esters, but also cationic emulsifiers, such as mono-, di- or trialkyl quats and polymeric derivatives thereof.

In order to adjust the rheological properties of aqueous or solvent-containing emulsions or suspensions, a large number of different systems are given in the specialist literature. For example, cellulose ethers and other cellulose derivatives (e.g. carboxymethylcellulose, hydroxyethylcellulose), gelatin, starch and starch derivatives, sodium alginates, fatty acid polyethylene glycol esters, agar agar, tragacanth or dextrins, are known. The synthetic polymers used are various materials, such as, for example, polyvinyl alcohols, polyacrylamides, polyvinylamides, polysulfonic acids, polyacrylic acid, polyacrylic esters, polyvinylpyrrolidone, polyvinyl methyl ether, polyethylene oxides, copolymers of maleic anhydride and vinyl methyl ether, and diverse mixtures and copolymers of the abovementioned compounds, including their various salts and esters. These polymers can, if desired, be crosslinked or uncrosslinked.

The emulsions can be prepared in a known manner, for example by hot, hot/cold or PIT emulsification.

EXAMPLE 1

Preparation of Ethoxylated (150 EO) Diglycerol, Esterified with 3 mol of Stearic Acid a) Preparation of Ethoxylated (150 EO) Diglycerol The crude product (diglycerol) was admixed with a basic catalyst (NaOH) and then dried at 90-100° C./20 mbar for half an hour. Subsequently, at about 160° C. and a pressure of 5 bar, 150 mol of EO per mole of diglycerol were metered in over the course of 15 hours. At the end of the post-reaction time (about 2 hours), the product was cooled and degassed.

b) Preparation of Ethoxylated (150 EO) Polyglycerol-2 Tristearate 250.00 g of ethoxylated (150 EO) diglycerol were added to a stirred container (with $N_2$ introduction and water separator) and admixed with 1.26 g of alkylbenzenesulfonic acid (0.45% of the total mixture) and 0.67 g of hypophosphorous acid (0.24% of the total mixture). Then, 30.40 g of stearic acid (molar ratio of ethoxylated diglycerol:stearic acid=1:3) were added and the reaction mixture was heated to 230° C. with stirring.

After a reaction time of 30 hours, a OH number of 0.45 mg of KOH/g was achieved.

The product is a soft wax with a melting point of 38° C. The other test products shown in table 1 were prepared starting from diglycerol or tetraglycerol by reaction of EO and stearic acid or oleic acid in an analogous manner.

The excellent thickening performance of the alkoxylated polyglycerol ester in an aqueous surfactant system is compared in table 1 with the thickening capacity of conventional thickeners.

TABLE 1

Measured viscosities in mPa · s of an aqueous surfactant solution comprising 15% by weight of a mixture of $C_{12}/C_{14}$-alkyl diglycol ether sulfate Na and cocoamidopropylbetaine (weight ratio 8:2) and thickener in the given amount, adjusted to pH 6 with citric acid/NaOH.

| Thickener | 1.5% by wt. | 2% by wt. | 2.5% by wt. | 3% by wt. | 3.5% by wt. | 4% by wt. | 4.5% by wt. | 5% by wt. |
|---|---|---|---|---|---|---|---|---|
| PEG 6000 distearate | — | — | 1110 | 4670 | 20000 | 29700 | 46000 | 81500 |
| PEG 120 methyl-glucose dioleate | 26 | 138 | 1650 | 8700 | 27200 | 12900 | — | |
| Diglycerol + 150 EO tristearate | 7800 | 69000 | 163000 | >200000 | | | | |
| Polyglycerol −4 + 150 EO pentastearate | | 670 | 9300 | 80000 | 144000 | >200000 | >200000 | >200000 |
| Diglycerol + 150 EO distearate | — | 290 | 4300 | 24000 | 51000 | 111000 | 180000 | >200000 |

The application examples below serve to illustrate the subject-matter of the invention in more detail without limiting it thereto. The percentages are percentages by weight.

Shampoo/shower preparation formulations

| a) | ®Genapol LRO liq., washing-active substance (WS) 28% ($C_{12/14}$-alkyl diglycol ether sulfate, Na) | 44.4% |
|---|---|---|
| | ®Genagen CAB 818, WS 30% (cocoamidopropylbetaine) | 10.0% |
| | Water | ad 100% |
| | Diglycerol + 150 EO distearate | 2.57% |
| | Citric acid/NaOH | |

The formulation has a viscosity of 4 300 mPas.

| b) | Genapol LRO liq., WS 28% ($C_{12/14}$-alkyl diglycol ether sulfate, Na) | 44.4% |
|---|---|---|
| | Genagen CAB 818, WS 30% (cocoamidopropylbetaine) | 10.0% |
| | Water | ad 100% |
| | Diglycerol + 150 EO tristearate | 1.5% |
| | Citric acid/NaOH | |

The formulation has a viscosity of 3 800 mPas.

| c) | Genapol LRO liq., WS 28% (C12/14-alkyl diglycol ether sulfate, Na) | 44.4% |
|---|---|---|
| | Genagen CAB 818, WS 30% (cocoamidopropylbetaine) | 10.0% |
| | Water | ad 100% |
| | Tetraglycerol + 150 EO distearate | 5.5% |
| | Citric acid/NaOH | |

The formulation has a viscosity of 4 100 mPas.

| d) | Genapol LRO liq., WS 28% ($C_{12/14}$-alkyl diglycol ether sulfate, Na) | 44.4% |
|---|---|---|
| | Genagen CAB 818, WS 30% (cocoamidopropylbetaine) | 10.0% |
| | Water | ad 100% |
| | Tetraglycerol + 150 EO tristearate | 4.0% |
| | Citric acid/NaOH | |

The formulation has a viscosity of 2 680 mPas.

| e) | Genapol LRO liq., WS 28% ($C_{12/14}$-alkyl diglycol ether sulfate, Na) | 44.4% |
|---|---|---|
| | Genagen CAB 818, WS 30% (cocoamidopropylbetaine) | 10.0% |
| | Water | ad 100% |
| | Tetraglycerol + 150 EO tetrastearate | 2.5% |
| | Citric acid/NaOH | |

The formulation has a viscosity of 4 200 mPas.

| f) | Genapol LRO fl., WS 28% ($C_{12/14}$-alkyl diglycol ether sulfate, Na) | 44.4% |
|---|---|---|
| | Genagen CAB 818, WS 30% (cocoamidopropylbetaine) | 10.0% |
| | Water | ad 100% |
| | Tetraglycerol + 150 EO pentastearate | 2.5% |
| | Citric acid/NaOH | |

The formulation has a viscosity of 4 300 mPas.

The viscosity was measured at 20° C. using a Brookfield viscometer model RVT at 20 rpm.

The invention claimed is:

1. A cosmetic or pharmaceutical preparation in the form of a shampoo, shower preparation, shower gel, foam bath, gel, lotion, cream or ointment comprising an oxalkylated polyglycerol ester of formula (1) or a mixture thereof

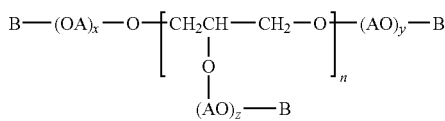
(1)

wherein
  A is a group of the formula —$C_2H_4$—,
  B is hydrogen or a group of the formula —COR,
  where at least one symbol B is a group of the formula —COR, R is $C_7$-$C_{21}$-alkyl, $C_7$-$C_{21}$-hydroxyalkyl or $C_2$-$C_{21}$-alkenyl,
  n is a number from 1.8 to 5 and
  x, y and z are numbers from 0 to 100, where the sum of x, y and z is 130 to 170.

2. The cosmetic or pharmaceutical preparation of claim 1, further comprising:
  a) 7 to 30 weight percent of an anionic surfactant;
  b) 1 to 10 weight percent of a cationic surfactant
  c) 1 to 20 weight percent of a non-ionic surfactant; and
  d) 0.5 to 20 weight percent of an amphoteric surfactant.

3. The cosmetic or pharmaceutical preparation of claim 1, wherein said preparation comprises 0.05 to 10% by weight of the oxalkylated polyglycerol ester of the formula (1).

4. The cosmetic or pharmaceutical preparation of claim 1, wherein said preparation is flowable at room temperature.

5. A method for treating human skin comprising contacting said skin with the cosmetic or pharmaceutical preparation comprising an oxalkylated polyglycerol ester of formula (1) or a mixture thereof

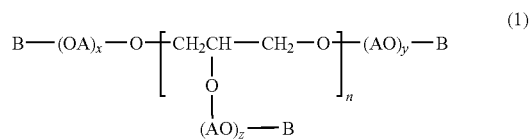
(1)

wherein
  A is a group of the formula —$C_2H_4$—,
  B is hydrogen or a group of the formula —COR,
  where at least one symbol B is a group of the formula —COR, R is $C_7$-$C_{21}$-alkyl, $C_7$-$C_{21}$-hydroxyalkyl or $C_2$-$C_{21}$-alkenyl,
  n is a number from 1.8 to 5 and
  x, y and z are numbers from 0 to 100, where the sum of x, y and z is 130 to 170.

6. A cosmetic or pharmaceutical preparation comprising an oxalkylated polyglycerol ester of formula (1) or a mixture thereof

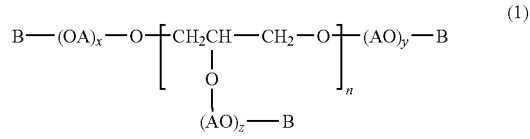
(1)

wherein
  n is 2,
  A is a group of the formula —$C_2H_4$—,
  B is hydrogen or a group of the formula —COR,
  wherein R is linear $C_{17}$ alkyl and where three of the four symbols B are a group of the formula —COR wherein R is linear $C_{17}$ alkyl and one of the four symbols B is hydrogen and
  x, y and z are numbers from 0 to 100, where the sum of x, y and z is 150.

* * * * *